United States Patent
Hagiwara

(10) Patent No.: US 7,894,567 B2
(45) Date of Patent: Feb. 22, 2011

(54) X-RAY TOMOGRAPHY APPARATUS AND ARTIFACT REDUCING METHOD

(75) Inventor: Akira Hagiwara, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 625 days.

(21) Appl. No.: 11/924,432

(22) Filed: Oct. 25, 2007

(65) Prior Publication Data

US 2008/0118022 A1 May 22, 2008

(30) Foreign Application Priority Data

Oct. 27, 2006 (JP) ............................. 2006-292155

(51) Int. Cl.
*A61B 6/03* (2006.01)
(52) U.S. Cl. ....................................................... 378/4
(58) Field of Classification Search ................... 378/4; 382/128–131, 275

See application file for complete search history.

(56) References Cited

U.S. PATENT DOCUMENTS 5,537,485 A 7/1996 Nishikawa et al.

(Continued)

FOREIGN PATENT DOCUMENTS

EP 0962888 A2 12/1999

(Continued)

OTHER PUBLICATIONS

Keselbrener et al., Nonlinear Filters Applied on Computerized Axial Tomography: Theory and Phantom Images, Medical Physics, Jul. 1, 1992, pp. 8.

(Continued)

*Primary Examiner*—Edward J Glick
*Assistant Examiner*—John M Corbett
(74) *Attorney, Agent, or Firm*—Armstrong Teasdale LLP

(57) ABSTRACT

The present invention provides an X-ray tomography apparatus that positively extracts artifacts without decreasing directional resolution thereby to reduce the artifacts. The X-ray tomography apparatus includes scan device for exposing X rays to a subject while at least one of a gantry and a table is being moved along a body-axis direction of the subject, thereby to create projection data of the subject, CT value change specifying device for specifying the amount of change in CT value in the body-axis direction between a plurality of tomographic images obtained by backprojecting the projection data, with respect to each of pixel areas contained in the tomographic images, image processing condition selecting device for selecting an image processing condition for performing an image process for reducing artifacts, according to the specified amount of change in CT value, and artifact reducing device for performing an image process using the image processing condition selected by the image processing condition selecting device.

20 Claims, 12 Drawing Sheets

U.S. PATENT DOCUMENTS

| | | | |
|---|---|---|---|
| 5,712,889 | A | 1/1998 | Lanzara et al. |
| 5,828,725 | A | 10/1998 | Levinson |
| 6,373,920 | B1 | 4/2002 | Hsieh |
| 6,463,118 | B2 | 10/2002 | Besson |
| 7,359,476 | B2 | 4/2008 | Hagiwara |
| 2005/0053187 | A1* | 3/2005 | Hagiwara ............ 378/4 |
| 2005/0226365 | A1 | 10/2005 | Taguchi |
| 2006/0029285 | A1 | 2/2006 | Hein et al. |
| 2006/0285737 | A1* | 12/2006 | Hamill et al. ........ 382/131 |
| 2007/0195931 | A1* | 8/2007 | Ohishi ............ 378/98.2 |
| 2008/0130823 | A1* | 6/2008 | Hagiwara ............ 378/4 |

FOREIGN PATENT DOCUMENTS

| | | |
|---|---|---|
| JP | 2003-325502 | 11/2003 |
| JP | 2005080918 | 3/2005 |

OTHER PUBLICATIONS

Jiang Hsieh, Adaptive Interpolation Approach for Multi-slice Helical CT Reconstruction, Proceedings of the Spie—The International Society for Optical Engineering, May 1, 2003, pp. 8, vol. 5032.

Silver et al., Windmill Artifact in Multi-slice Helical CT, Proceedings of the Spie—The International Society for Optical Engineering, Feb. 17, 2003, pp. 10, vol. 5032.

Pitas et al., Nonlinear Digital Filters, 9.7—Two-component Image Filtering, Nonlinear Digital Filters: Principles and Applications, Dordrecht: Kluwer Academic Publishers, Jan. 1, 1990, pp. 284-290.

International Search Report, NL1034577, dated Nov. 18, 2008, pp. 15.

International Search Report, NL1034578, dated Nov. 11, 2008, pp. 20.

Xiangyang Tang et al., Cone beam volume CT image artifacts caused by defective cells in x-ray flat panel imagers and the artifact removal using a wavelet-analysis-based algorithm, Medical Physics, May 1, 2001, pp. 812-825.

Gary A. Mastin, Adaptive Filters for Digital Image Noise Smoothing: An Evaluation, Computer Vision Graphics and Image Processing, Academic Press, Jul. 1, 1985, pp. 103-121.

Roland T. Chin et al., Quantitative Evaluation of Some Edge-Preserving Noise-Smoothing Techniques, Computer Vision Graphics and Image Processing, Academic Press, Jul. 1, 1983, pp. 67-91.

Marc Kachelriess et al., Generalized multi-dimensional adaptive filtering for conventional and spiral single-slice, multi-slice, and cone-beam CT, Medical Physics, Apr. 1, 2001, pp. 475-490.

* cited by examiner

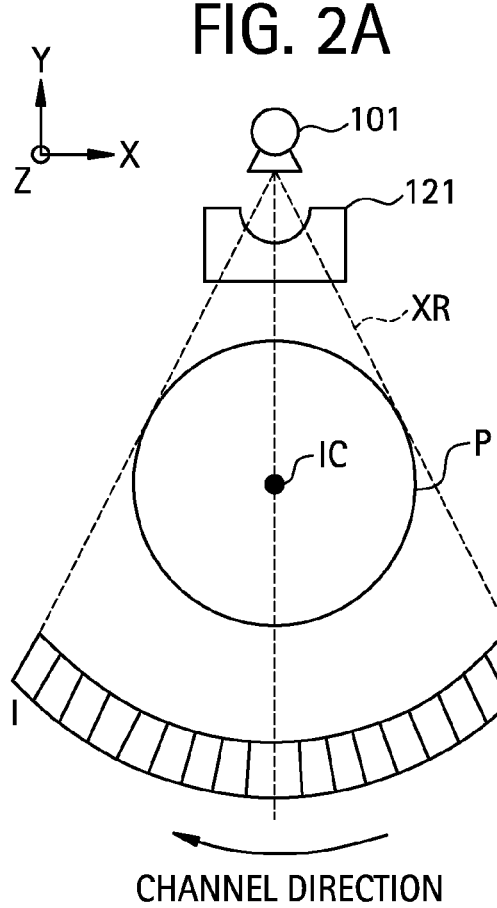
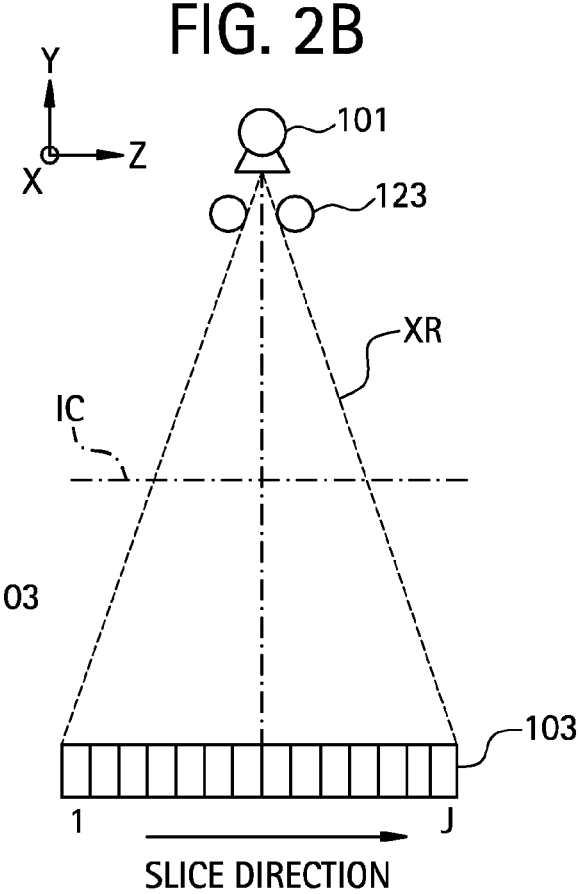

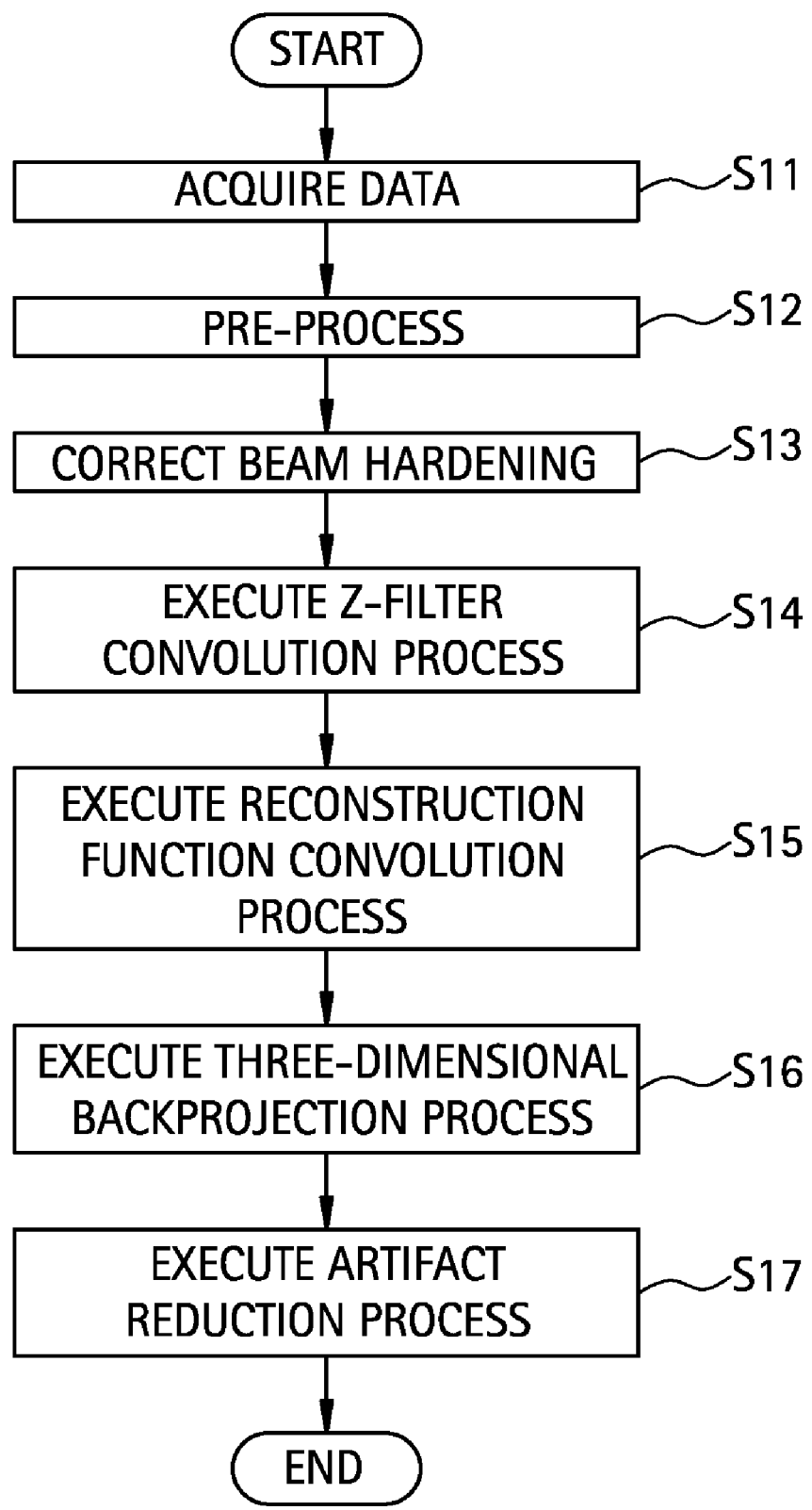

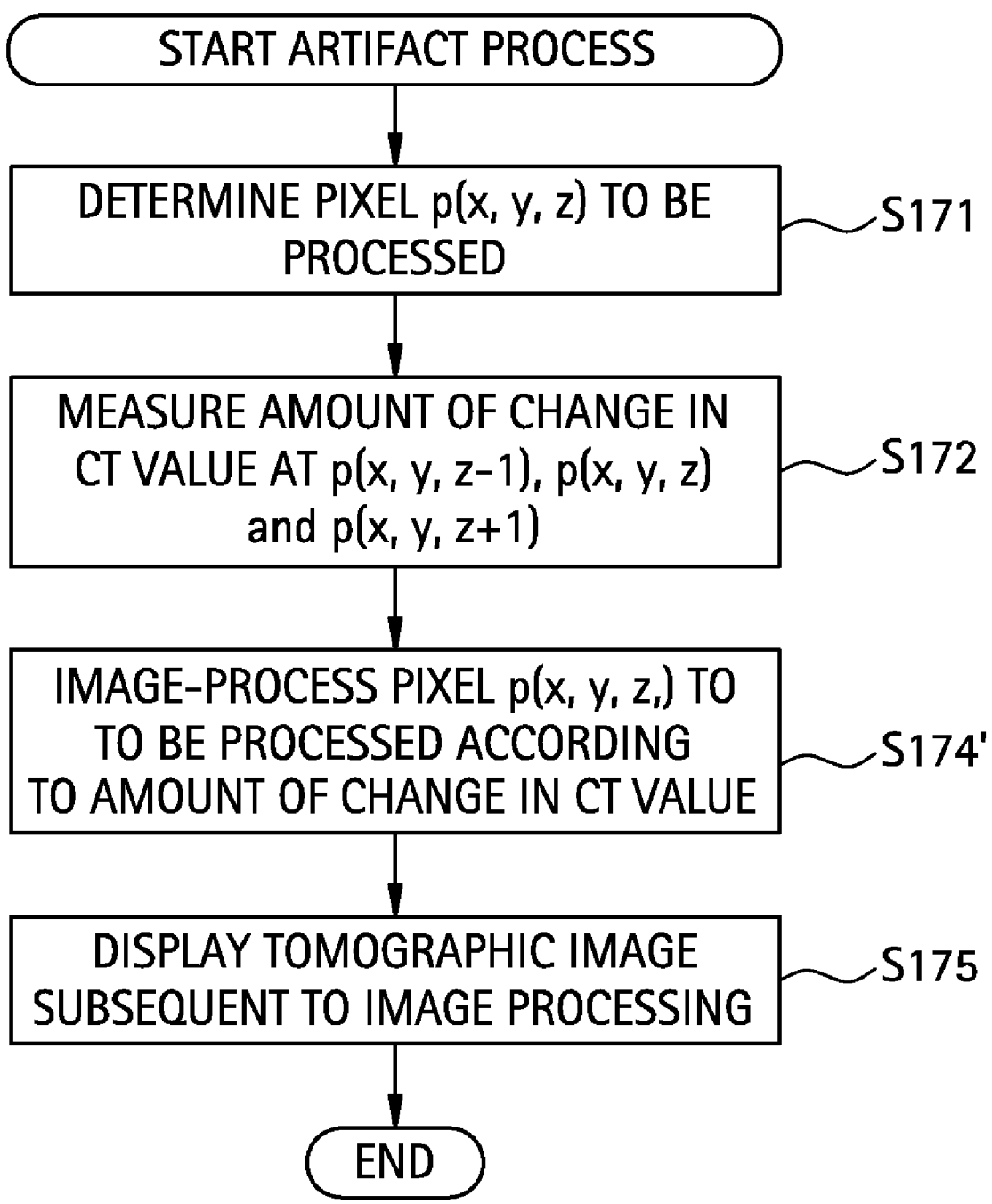

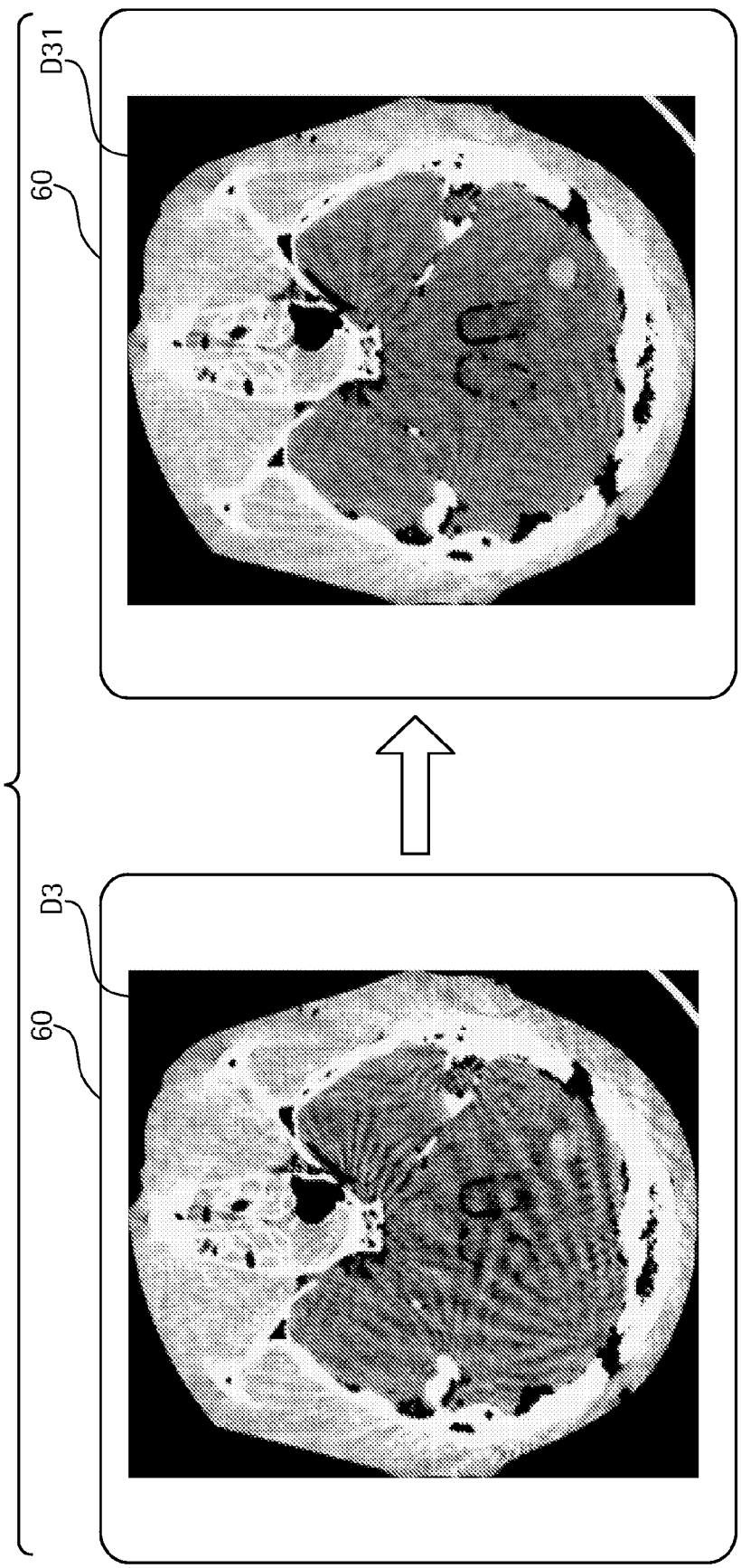

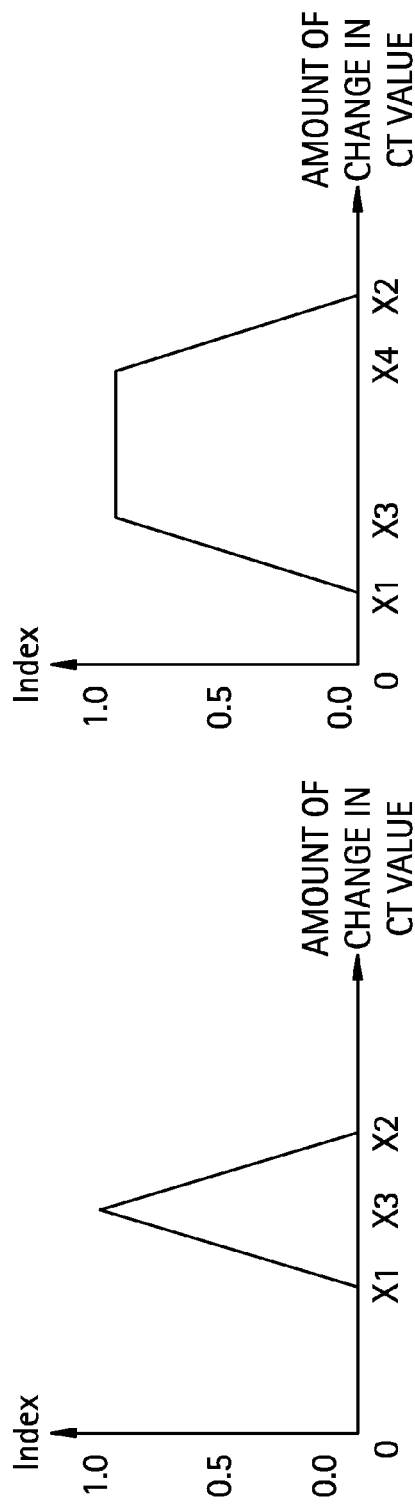
FIG. 7A
FIG. 7B
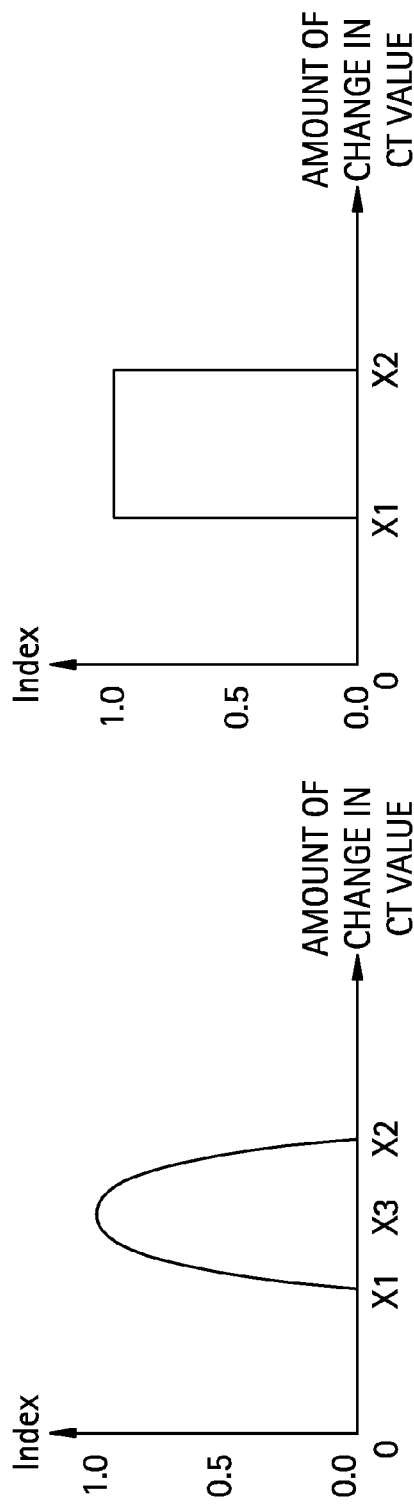
FIG. 7C
FIG. 7D

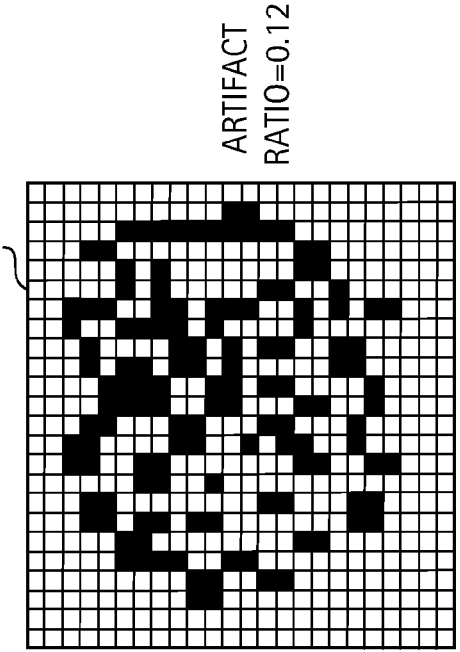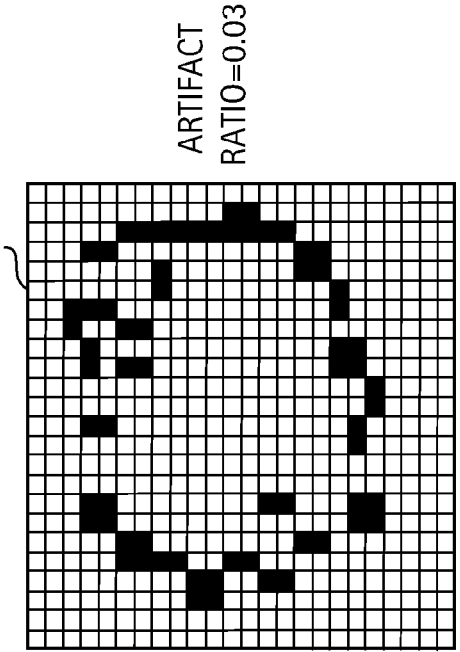
FIG. 9A-2  FIG. 9B-2
ARTIFACT RATIO=0.12  ARTIFACT RATIO=0.03
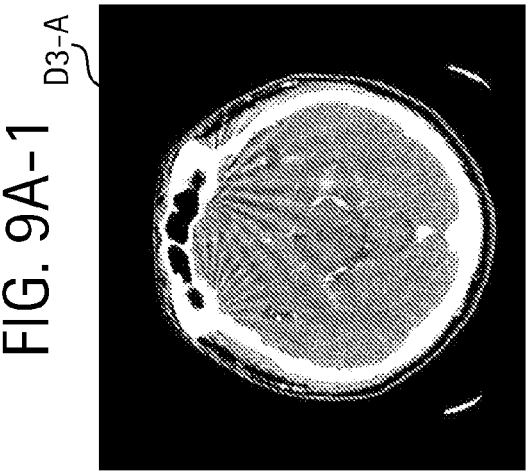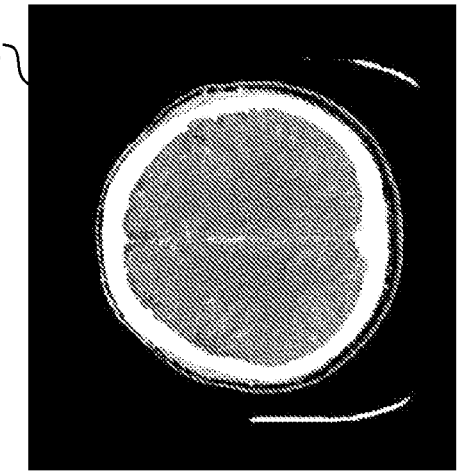
FIG. 9A-1  FIG. 9B-1

X-RAY TOMOGRAPHY APPARATUS AND ARTIFACT REDUCING METHOD

CROSS REFERENCE TO RELATED APPLICATIONS

This application claims the benefit of Japanese Application No. 2006-292155 filed Oct. 27, 2006.

BACKGROUND OF THE INVENTION

The present invention relates to an X-ray tomography apparatus which displays tomographic images having less influence over artifacts such as a cone-beam artifact, a windmill artifact, etc., at an X-ray CT (Computed Tomography) apparatus or the like, and an artifact reducing method thereof.

In a multi-slice X-ray computer tomography (X-ray CT) apparatus, the number of slices is now increasing to 64 or 256. There have been known various cone-beam image reconstruction algorithms using a helical scan of the X-ray CT apparatus. However, one problem common among the cone-beam image reconstruction algorithms is that a sampling interval in a body-axis direction (called also z direction or slice direction) of a subject is insufficient. These algorithms run counter to Nyquist's theorem and cause vortical windmill-like artifacts within each reconstructed image due to high-frequency components. That is, when the resolution of a detector is insufficient for a structure and a helical pitch is made larger at the helical scan, interpolation calculations cannot be carried out ideally and hence the windmill-like artifacts occur on an image.

In order to reduce such windmill-like artifacts, multi-point interpolation is performed in the z direction to reduce the width of a fluctuation of a target signal, thereby casting the windmill-like artifacts into the shade. In a patent Japanese Unexamined Patent Publication No. 2003-325502, for example, an interpolation process is performed in a z direction upon execution of a reconstruction function convolution process thereby to attempt to reduce windmill-like artifacts.

SUMMARY OF THE INVENTION

In the method for performing the multi-point interpolation in the z direction to reduce the artifacts, however, interpolation is effected even on image areas with no artifacts developed therein, thus leading to a reduction in resolution in a Z direction, whereby a distinct tomographic image cannot be obtained by a more increase in resolution.

Therefore, the present invention aims to provide an X-ray tomography apparatus that positively extracts artifacts without decreasing resolution in a Z direction thereby to reduce the artifacts, and an artifact reducing method thereof.

In the present invention, artifacts are reduced only with respect to image areas each having the artifact developed therein, from a three-dimensionally back-projected tomographic image. The three-dimensionally back-projected tomographic image is used as it is with respect to a region free of the occurrence of the artifacts and the tomographic image is displayed. Therefore, a distinct tomographic image can be obtained with respect to the image area free of the occurrence of the artifacts without reducing resolution in a z direction.

An X-ray tomography apparatus according to a first aspect comprises scan device for exposing X rays to a subject while at least one of a gantry and a table is being moved along a body-axis direction of the subject, thereby to create projection data of the subject, CT value change specifying device for specifying an amount of change in CT value in the body-axis direction between a plurality of tomographic images obtained by backprojecting the projection data, with respect to each of pixel areas contained in the tomographic images, image processing condition selecting device for selecting an image processing condition for performing an image process for reducing artifacts, according to the specified amount of change in CT value, and artifact reducing device for performing an image process using the image processing condition selected by the image processing condition selecting device.

In the X-ray tomography apparatus according to the first aspect, the amount of change in CT value in the body-axis direction is specified with respect to each of the pixel areas of the backprojected tomographic images. An image processing condition is selected based on the specified amount of change in CT value. An image area with artifacts developed therein and an image area with no artifacts are determined based on the specified amount of change in CT value. If no artifacts occur, then an image processing condition that takes advantage of an image in that image area as it is selected. Image processing can be effected only on the image area with the artifacts developed therein such that the artifacts are reduced. Incidentally, the amount of change in CT value includes the average value of the change in CT value in the body-axis direction or the difference between the maximum and minimum values of the change in CT value in the body-axis direction.

The X-ray tomography apparatus according to a second aspect further includes artifact ratio calculating device for calculating a ratio at which each pixel area in which the amount of change in CT value is a predetermined range, is occupied within a predetermined area contained in each of the tomographic images, and determining device for determining that when the ratio is larger than a threshold value, an image process for reducing the artifacts is effected on the pixel area.

In the X-ray tomography apparatus according to the second aspect, although there is a high possibility that if the amount of change in CT value is of a predetermined range, then pixels having artifacts will exist, the amount of change in CT value might fall within the predetermined range depending upon an influence such as an imaging condition. Thus, the ratio at which a pixel area in which the amount of change in CT value is of a predetermined range, is occupied within a predetermined area contained in each of tomographic images, is calculated. If the ratio is low, then a pixel high in resolution as viewed in a body-axis direction is maintained as it is without performing an artifact reducing process. If the ratio is high, there is then a high probability of artifacts being developed. Therefore, image processing can be effected only on an image area with artifacts developed therein, of its tomographic image so as to reduce the artifacts.

In the X-ray tomography apparatus according to a third aspect, the image process of the artifact reducing device includes a process for multiplying the image areas of the plural tomographic images by weighting factors each selected as the image processing condition and adding the results of multiplication.

In the constitution of the third aspect, it is determined that when the amount of change in CT value is of a predetermined range, an image area with artifacts developed therein exists. In relation to each image area with the artifacts developed therein, a plurality of pixel areas in a body-axis direction are multiplied by weighting factors and the results of multiplication are added together, thereby reducing the artifacts in the pixel area of each tomographic image.

In the X-ray tomography apparatus according to a fourth aspect, the image processing condition selecting device sets the weighting factor to be larger than 0 when the amount of change in CT value is of the predetermined range.

In the constitution of the fourth aspect, a plurality of pixel areas in a body-axis direction are multiplied by weighting factors set larger than 0 with respect to the image area with the artifacts developed therein, and thereby artifacts in the pixel area of each tomographic image are reduced.

In a fifth aspect, the image processing condition selecting device changes the weighting factor according to the number of the pixel areas in the body-axis direction.

In the constitution of the fifth aspect, the weighting factor can be changed based on the number of the pixel areas in the body-axis direction, corresponding to, for example, 3 in the case of one slice image in the neighborhood of a target area, and 2n+1 in the case of n slice images in the neighborhood thereof.

In the X-ray tomography apparatus according to a sixth aspect, the image processing condition selecting device changes the weighting factor according to the amount of change in CT value in the third or fourth aspect.

In the constitution of the sixth aspect, the weighting factor can be changed according to the amount of change in CT value, e.g., the amount of change such as 20 HU, 100 HU or the like. That is, suitable artifact reductions can respectively be made to an image area in which artifacts are strongly developed, and an image area in which artifacts are weakly developed.

In the X-ray tomography apparatus according to a seventh aspect, the CT value change specifying device determines an index value according to the amount of change in CT value.

In the constitution of the seventh aspect, an index value is determined from the amount of change in CT value. Thus, the index value is capable of distinguishing between an image area with artifacts developed therein and an image area with no artifacts. Using the index value makes it easy to set image processing.

In the X-ray tomography apparatus according to an eighth aspect, the plural pixel areas in the body-axis direction are multiplied by weighting factors in relation to the pixel areas according to the index value and the results of multiplication are added together.

In the constitution of the eighth aspect, the weighting factors are changed with respect to the plural pixel areas in the body-axis direction according to the index value and they are multiplied by one another, thereby making it possible to reduce artifacts in the pixel area of each tomographic image. That is, suitable artifact reductions can respectively be made to an image area in which artifacts are strongly developed, and an image area in which artifacts are weakly developed.

In a ninth aspect, when the amount of change in CT value ranges from 3 HU to 300 HU in the second or fourth aspect, the artifact reducing device reduces artifacts with respect to each pixel area.

It is judged that when the amount of change in CT value ranges from 3 HU to 300 HU, the artifacts are being developed. Assuming that the amount of change in CT value is, for example, 300 HU or more, it means a region varied from a soft tissue to a bone or the like, or a region varied vice versa. If the amount of change in CT value is 3 HU or less, it then means that the soft tissue or the bone is continuous in plural slice directions. On the other hand, the change in CT value from 3 HU to 300 HU means that a windmill artifact or a cone-beam artifact is being developed.

In the X-ray tomography apparatus according to a tenth aspect, each pixel area comprises one pixel or plural pixels.

In the tenth aspect, a pixel area of a target tomographic image can be processed as one pixel or plural pixels.

A method of reducing artifacts of tomographic images by X rays, according to an eleventh aspect, comprises the steps of specifying an amount of change in CT value in a body-axis direction between a plurality of tomographic images obtained by backprojecting projection data of a subject obtained by exposing X rays to the subject while at least one of a gantry and a table is being moved along the body-axis direction of the subject, with respect to each of pixel areas contained in the tomographic images, selecting an image processing condition for performing an image process for reducing the artifacts, according to the specified amount of change in CT value, and performing an image process using the selected image processing condition.

In the artifact reducing method according to the eleventh aspect, the amount of change in CT value in the body-axis direction is specified with respect to each of the pixel areas of the backprojected tomographic images. The image processing condition is selected based on the amount of change in CT value. That is, a decision is made based on the specified amount of change in CT value, as to an image area with artifacts developed therein and an image area with no artifacts. If it is found that the artifacts have been developed, then an image processing condition which takes advantage of its image as it is, is selected. Image processing can be effected only on the image area with the artifacts developed therein such that the artifacts are reduced.

The artifact reducing method according to a twelfth aspect further comprises the steps of calculating a ratio at which each pixel area in which the amount of change in CT value is a predetermined range, is occupied within a predetermined area contained in each of the tomographic images, and determining that when the ratio is larger than a threshold value, the image process for reducing the artifacts is effected on each of the pixel areas.

Although there is a high possibility that if the amount of change in CT value is of a predetermined range, then pixels having artifacts will exist, the amount of change in CT value might fall within the predetermined range depending upon an influence such as an imaging condition. Thus, the artifact reducing method according to the twelfth aspect calculates the ratio at which the pixel area in which the amount of change in CT value is of the predetermined range, is occupied within the predetermined area contained in each of the tomographic images. If the ratio is low, then a pixel high in resolution as viewed in the body-axis direction is maintained as it is without performing an artifact reducing process. If the ratio is high, there is then a high probability of artifacts being developed. Therefore, image processing can be effected only on an image area with the artifacts developed therein, of its tomographic image so as to reduce the artifacts.

In the artifact reducing method according to a thirteenth aspect, the image process for reducing the artifacts includes a process for multiplying the image areas of the tomographic images by weighting factors each selected as the image processing condition and adding the results of multiplication.

In the artifact reducing method of the thirteenth aspect, it is determined that when the amount of change in CT value is of a predetermined range, an image area with artifacts developed therein exists. With respect to each image area with the artifacts developed therein, a plurality of pixel areas in a body-axis direction are multiplied by weighting factors and the results of multiplication are added together, thereby reducing the artifacts in the pixel area of each tomographic image.

In the artifact reducing method for tomographic images by X rays, according to a fourteenth aspect, the image processing condition selecting step sets the weighting factor to be larger than 0 when the amount of change in CT value is of the predetermined range.

In the artifact reducing method according to the fourteenth aspect, a plurality of pixel areas in a body-axis direction are multiplied by weighting factors set larger than 0 in relation to the image area with the artifacts developed therein, and thereby the artifacts in the pixel area of each tomographic image are reduced.

In the artifact reducing method according to a fifteenth aspect, the weighting factor is changed according to the number of the pixel areas in the body-axis direction.

In the artifact reducing method according to the fifteenth aspect, the weighting factor can be changed based on the number of the pixel areas in the body-axis direction, corresponding to, for example, 3 in the case of one slice in the neighborhood of a target area, and 2n+1 in the case of n slices in the neighborhood thereof.

In the artifact reducing method according to a sixteenth aspect, the weighting factor is changed according to the amount of change in CT value.

In the constitution of the sixteenth aspect, the weighting factor can be changed according to the amount of change in CT value, e.g., the amount of change such as 40 HU, 60 HU or the like. That is, suitable artifact reductions can respectively be made to an image area in which artifacts are strongly developed, and an image area in which artifacts are weakly developed.

In the artifact reducing method according to a seventeenth aspect, an index value is determined according to the specified amount of change in CT value.

In the artifact reducing method of the seventeenth aspect, an index value is determined from the amount of change in CT value. Thus, the index value is capable of distinguishing between an image area with artifacts developed therein and an image area with no artifacts. Using the index value makes it easy to set image processing.

In the artifact reducing method according to an eighteenth aspect, the weighting factor is changed according to each region of the subject.

In the artifact reducing method according to the eighteenth aspect, the weighting factor may be changed depending upon the head, neck, chest and the like even though the same amount of change in CT value is taken. This is because the type of soft tissue, the thickness of the bone, the complexity of the shape and the like vary according to subject' regions.

In the artifact reducing method according to a nineteenth aspect, an artifact is reduced with respect to each of the pixel areas when the amount of change in CT value ranges from 3 HU to 300 HU.

In the constitution of the nineteenth aspect, it is judged that when the amount of change in CT value ranges from 3 HU to 300 HU, artifacts have been developed. When the amount of change in CT value is 300 HU or more, for example, it means a portion or region that has changed from a soft tissue to the bone or the like or a region that has changed vice versa. If the amount of change in CT value is 3 HU or less and 10 HU or less depending upon imaging circumstances, it then means that the soft tissue or the bone is continuous in plural slice directions. In a pixel area transitioned from the soft tissue to the bone or from the bone to the soft tissue in reverse and a pixel area transitioned from the lung to a soft tissue or vice versa, the amount of change ranging from over 200 HU to over 300 HU exists. Therefore, on the other hand, it can be estimated from the change in CT value from 3 HU to 300 HU that a windmill artifact or a cone-beam artifact has been developed.

In the artifact reducing method according to a twentieth aspect, when the amount of change in CT value ranges from 0 HU to 300 HU, an artifact is reduced with respect to each of the pixel areas and noise is reduced with respect to the pixel area.

In the constitution of the twentieth aspect, a reduction in noise is carried out when the amount of change in CT value is 3 HU or less. It means that if the amount of change in CT value is 3 HU or less, a soft tissue or a bone is continuous in plural slice directions. However, when the amount of change in CT value is 3 HU or less, weighting is effected on plural slice images so that a noise reduction of each tomographic image is also carried out.

According to an X-ray tomography apparatus of the present invention and an artifact reducing method thereof, artifacts are reduced only with respect to image areas each having the artifact developed therein, from a three-dimensionally back-projected tomographic image. A tomographic image in which the three-dimensionally back-projected tomographic image is used as it is with respect to a region free of the occurrence of the artifacts, can be displayed.

BRIEF DESCRIPTION OF THE DRAWINGS

FIGS. 2(a) and 2(b) are diagrams showing geometrical layouts illustrative of an X-ray tube 10 and a multi-row X-ray detector 103.

FIG. 3 is a flowchart schematically showing a tomographic image photographing operation of the X-ray CT apparatus 10 of the present invention.

FIGS. 4(a) and 4(b) are flowcharts for reducing artifacts after determination of backprojection data D3.

FIG. 6 is an example in which a tomographic image D3 (x, y, z) prior to execution of an artifact reduction process and a tomographic image D31 (x, y, z) subjected to the artifact reduction process are displayed on a display 60.

FIGS. 7(a), 7(b), 7(c), and 7(d) are diagrams showing index functions.

FIGS. 9(A1), 9(A2), 9(B1), and 9(B2) are diagrams showing tomographic images prior to being subjected to an artifact reduction process, of the head of a subject, and reconstruction areas P.

DETAILED DESCRIPTION OF THE INVENTION

Configuration of X-ray CT apparatus.

Figure 1:
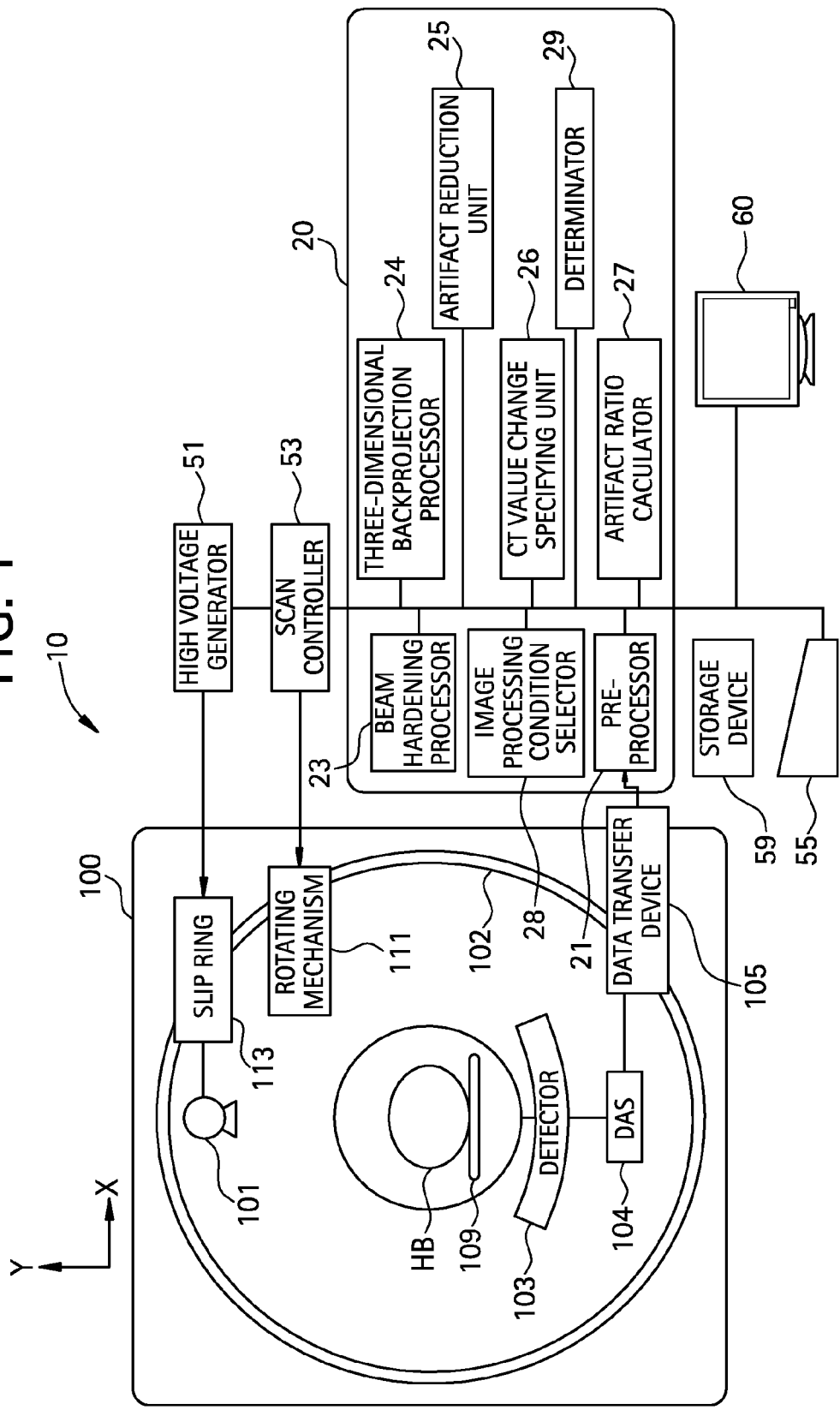
FIG. 1 is a block diagram showing a configuration of an X-ray CT apparatus 10 according to the present embodiment.

FIG. 1 is a block diagram showing a configuration of an X-ray computed tomography apparatus (X-ray CT apparatus) 10 according to the present embodiment. The X-ray tomography apparatus 10 is equipped with a gantry 100 and a table 109 for inserting a subject HB in an imaging area of the gantry 100. The table 109 is moved in a Z direction corresponding to the direction of a body axis of the subject HB. The gantry 100 has a rotating ring 102 and includes an X-ray tube 101 for exposing an X-ray beam XR shaped in the form of a cone beam to the rotating ring 102, and a multi-row X-ray detector 103 disposed opposite to the X-ray tube 101. The multi-row X-ray detector 103 detects X rays transmitted through the subject HB.

The multi-row X-ray detector 103 comprises scintillators and photodiodes. A data acquisition circuit 104 generally called DAS (data acquisition system) is connected to the multi-row X-ray detector 103. An I-V converter for converting a current signal for each channel of the multi-row X-ray detector 103 to a voltage, an integrator for periodically integrating the voltage signal in sync with an X-ray irradiation cycle or period, a preamplifier for amplifying a signal outputted from the integrator, and an analog-to-digital converter for converting a signal outputted from the preamplifier to a digital signal are provided for each channel in the data acquisition circuit 104. Digital signals sent from the data acquisition circuit 104 are transmitted to an image processing section or apparatus 20 through a data transfer device 105.

A high voltage generator 51 for supplying a voltage to the X rays is provided on the operation console side. The high voltage generator 51 periodically generates a high voltage and supplies the high voltage to the X-ray tube 101 through a slip ring 113.

A scan controller 53 on the operation console side executes a plurality of scan patterns such as an axial scan, a helical scan, a variable pitch helical scan. The axial scan is a scan method for rotating the X-ray tube 101 and the multi-row X-ray detector 103 each time the table 109 is moved by a predetermined pitch in the Z-axis direction thereby to obtain or acquire projection data. The helical scan is a scan method for moving the table 109 at a predetermined velocity in a state in which the X-ray tube 101 and the multi-row X-ray detector 103 are being rotated, thereby to acquire raw data. The variable pitch helical scan is a scan method for varying the velocity of the table 109 while the X-ray tube 101 and the multi-row X-ray detector 103 are being rotated by a rotating mechanism 111 in a manner similar to the helical scan thereby to acquire raw data. The scan controller 53 drives the rotating mechanism 111 in sync with the high voltage generator 51 and exercises control over scans such as periodic acquisition of raw data by the data acquisition circuit 104, etc.

An input device 55 comprises a keyboard or a mouse that receives an input from an operator. A storage device 59 stores programs, X-ray detector data, projection data and X-ray tomographic images therein. The image processing apparatus 20 effects a pre-process, an image reconstruction process, a post-process and the like on the projection data sent from the data acquisition circuit 104. A display 60 displays an operation screen and displays an image-reconstructed tomographic image.

Configuration of image processing section.

The image processing section or apparatus 20 includes a pre-processor 21, a beam hardening processor 23, a three-dimensional backprojection processor 24, an artifact reduction unit 25, a CT value change specifying unit 26, an artifact ratio calculator 27, an image processing condition selector 28 and a determinator 29.

The pre-processor 21 corrects channel-to-channel sensitivity ununiformity with respect to the raw data acquired by the data acquisition circuit 104 and executes a pre-process such as an X-ray dosage correction for correcting an extreme reduction in signal strength or a signal omission due to an X-ray strong absorber, principally, a metal portion. Incidentally, data done with the pre-process is called projection data in the present embodiment.

The beam hardening processor 23 effects correction processing on beam hardening of the projection data. The beam hardening is of a phenomenon that the absorption of X rays changes due to a penetration or transmission thickness even in the case of the same material and thereby a CT value (luminance) on each CT image varies. Particularly, it means that an energy distribution of radiation transmitted through a subject is biased to the high energy side. Therefore, the beam hardening is corrected in a slice direction of the projection data and a channel direction thereof.

The three-dimensional backprojection processor 24 receives the projection data pre-processed by the pre-processor 21 and reconstructs images, based on the projection data. The projection data is subjected to fast-Fourier transform (FFT) for transforming it to a frequency domain and convoluted with a reconstruction function Kernel (j), followed by being subjected to inverse Fourier transform. The three-dimensional backprojection processor 24 effects a three-dimensional backprojection process on the projection data subjected to the convolution processing of the reconstruction function Kernel (j) to determine a tomographic image (xy plane) for each body-axis direction (Z direction) of the subject HB. The three-dimensional backprojection processor 24 allows the storage device 59 to store the tomographic image.

The artifact reduction unit 25 reads the tomographic image subsequent to the three-dimensional backprojection from the storage device 59 and performs an artifact reduction process. The artifact reduction unit 25 allows the storage device 59 to store the tomographic image reduced in artifact and causes the display 60 to display it.

The CT value change specifying unit 26 specifies the amount of change in CT value in the body-axis direction. This is because if the amount of change in CT value in the body-axis direction falls within a predetermined range, it can be then estimated that artifacts are being developed.

The artifact ratio calculator 27 calculates how an image area with artifacts developed therein makes up the proportion in the tomographic image or a subject' area of the tomographic image.

The image processing condition selector 28 selects what image processing condition is made when the artifact reduction unit 25 performs image processing to reduce the artifacts. The image processing condition selector 28 selects, for example, values for assigning weights to plural pixels as viewed in the body-axis direction.

The determinator 29 determines whether the artifact reduction unit 25 should perform the artifact reduction process from the ratio calculated by the artifact ratio calculator 27.

FIGS. 2(a) and 2(b) are diagrams showing geometrical layouts of the X-ray tube 101 and the multi-row X-ray detector 10. FIG. 2(a) is a diagram showing the geometrical layouts of the X-ray tube 101 and the multi-row X-ray detector 103 as viewed from an xy plane, and FIG. 2(b) is a diagram showing the geometrical layouts of the X-ray tube 101 and the multi-row X-ray detector 103 as viewed from a yz plane. An anode of the X-ray tube 101 generates an X-ray beam XR called a cone beam. When the direction of a central axis of the cone beam is parallel to a y direction, it is assumed to be a view angle 0°. The multi-row X-ray detector 103 has X-ray detector rows corresponding to J rows in the z-axis direction (slice direction), for example, 256 rows. Each of the X-ray detector rows has X-ray detector channels corresponding to I channels as viewed in the channel direction, e.g., 1024 channels. In FIG. 2(a), more X rays in the X-ray beam XR emitted from the X-ray focal point of the X-ray tube 101 are applied in the center of an image reconstruction area P by a beam forming X-ray filter 121, whereas lesser X rays in the X-ray beam XR are applied at portions around the image reconstruction area P. Thus, the X rays are absorbed into the subject HB existing inside the image reconstruction area P after spatial control on the X-ray dosage, and the transmitted X rays are acquired by the multi-row X-ray detector 103 as raw data.

In FIG. 2(b), the X-ray beam XR emitted from the anode of the X-ray tube 101 is controlled in the direction of slice thickness of a tomographic image by an X-ray collimator 123 and hence the X rays are absorbed into a subject HB existing in the vicinity of the central axis IC of rotation, and the penetrated X rays are acquired by the multi-row X-ray detector 103 as raw data. Each of the raw data acquired by the multi-row X-ray detector 103 after the X rays have been applied to the subject HB, is A/D-converted by the data acquisition circuit 104 as viewed from the multi-row X-ray detector 103, followed by being inputted to the image processor 20 via the data transfer device 105. The raw data inputted to the image processor 20 is processed by the image processor 20 in accordance with the corresponding program of the storage device 59 and image-reconstructed into a tomographic image, which is followed by being displayed on the display 60. Incidentally, although the multi-row X-ray detector 103 has been applied in the present embodiment, a two-dimensional X-ray area detector of a matrix structure typified by a flat panel X-ray detector can also be applied.

Operation flowchart for tomogram photography.

FIG. 3 is a flowchart showing the outline of a tomographic image photographing operation of the X-ray CT apparatus 10 of the present invention.

At Step S11, a helical scan is executed to rotate the X-ray tube 101 and the multi-row X-ray detector 103 about the subject HB and acquire data from the multi-row X-ray detector 103 while the table 109 is being linearly moved. A z-direction position Ztable (view) is added to raw data D (view, j, i) (where j=1 to ROW and i=1 to CH) expressed in a view angle view, a detector row number j and a channel number i, and the acquisition of data in a constant-velocity range is performed.

At Step S12, the raw data D0 (view, j, i) is subjected to a pre-process and converted to projection data. An offset correction, a logarithmic translation, an X-ray dosage correction and a sensitivity correction are performed.

At Step S13, a beam hardening correction is effected on the pre-processed projection data D01 (view, j, i) thereby to convert it into projection data D1 subjected to the beam hardening correction. The beam hardening correction at Step S13 can be performed by a multiplication computation of a polynomial, for example. Since, at this time, the independent beam hardening corrections can be performed every j row as viewed in the slice direction of the multi-row X-ray detector 103, it is possible to correct the difference in X-ray energy characteristic between the detectors placed every row if X-ray tube voltages are different according to imaging conditions.

At Step S14, a z-filter convolution process for applying filters in the slice direction (z direction) is effected on the projection data D1 subjected to the beam hardening correction, and the projection data D1 is converted into projection data D11 subjected to the filter convolution process. That is, the z-filter convolution process is effected on projection data of the multi-row X-ray detector 103 at each view angle and each data acquisition system. When row-direction filter coefficients are changed for every channel, slice thicknesses can be controlled depending upon the distance from an image reconstruction center.

At Step S15, a reconstruction function Kernel (j) is convolution-processed with respect to the projection data D11 subjected to the filter convolution process. That is, the fast Fourier transform (FFT) for transforming the projection data D11 subjected to the filter convolution process into a frequency domain is preformed, and the reconstruction function Kernel (j) is convolution-processed for the projection data D11. Then, the inverse Fourier transform is performed to transform it into projection data D2 (view, j, i) subjected to a reconstruction function convolution process. Since the convolution process for the reconstruction function Kernel (j) and the reconstruction functions independent of one another every j row of the multi-row X-ray detector 103 can be carried out, the differences between noise characteristics and between resolution characteristics every row can be corrected.

At Step S16, a three-dimensional backprojection process is effected on the projection data D2 (view, j, i) subjected to the reconstruction function convolution process to determine backprojection data D3 (x, y, z). An image to be image-reconstructed is three-dimensionally image-reconstructed on a plane, i.e., an xy plane orthogonal to the z axis. The following reconstruction area P is assumed to be parallel to the xy plane.

At Step S17, post-processes such as an artifact reduction process, CT value conversion and the like are effected on the backprojection data D3 (x, y, z) to obtain a tomographic image D31 (x, y, z). In the artifact reduction process, an image area in which artifacts are being developed, is detected from the amount of change in CT value as viewed in the Z direction. A filter process is effected only on the detected image area in which the artifacts are being produced. With respect to an image area with no artifacts, the backprojection data D3 (x, y, z) is used as the tomographic image D31 (x, y, z) as it is.

Operation flowchart for artifact processing.

FIG. 4 is a flowchart used for performing a reduction in artifacts after determination of the backprojection data D3 (x, y, z). FIG. 5 is a conceptual diagram showing pixels of tomographic images based on the backprojection data D3 (x, y, z) and pixel areas thereof. Incidentally, windmill artifacts or cone-beam artifacts can be reduced by the present flowchart.

Figure 4A:
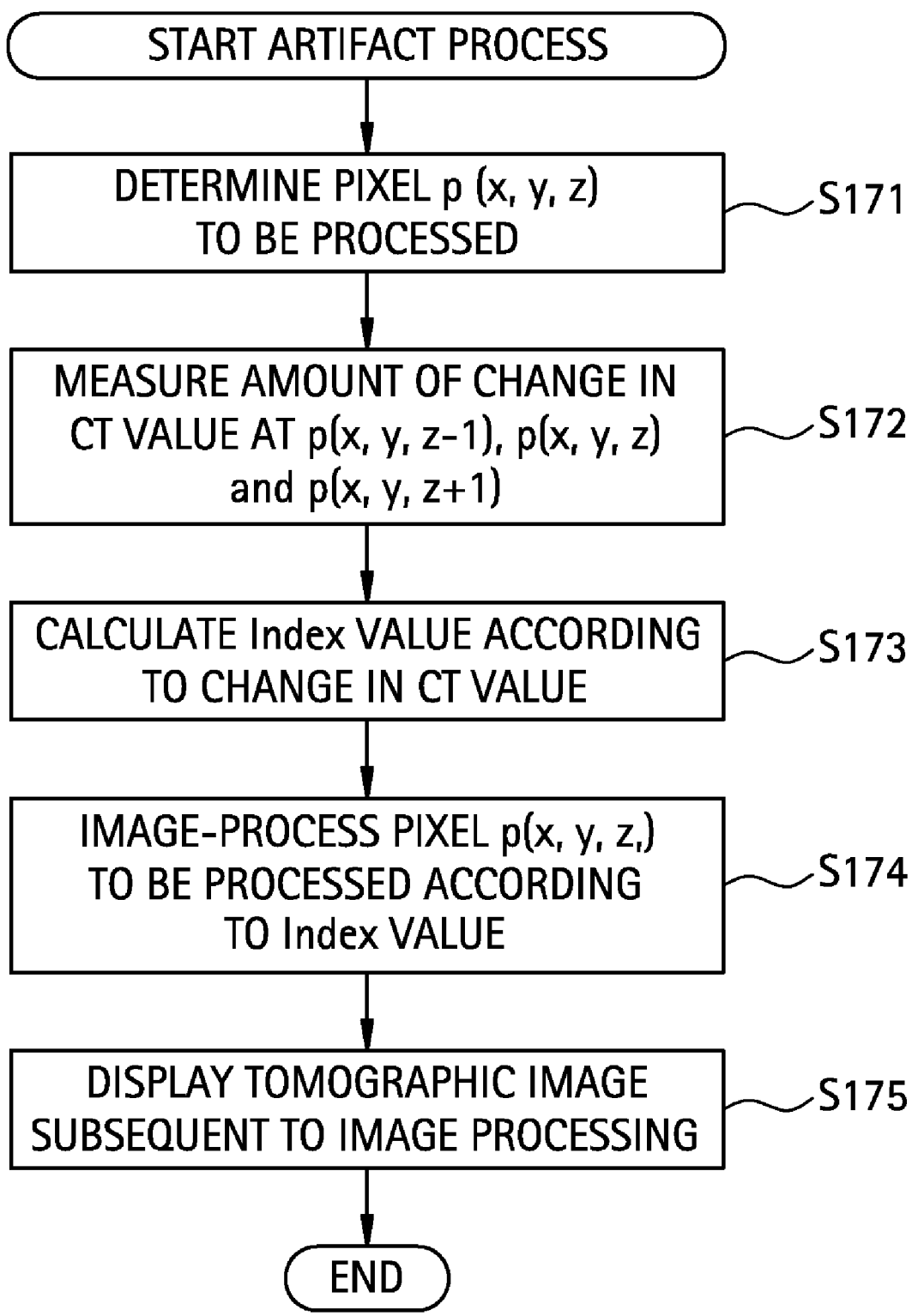
Figure 5B:
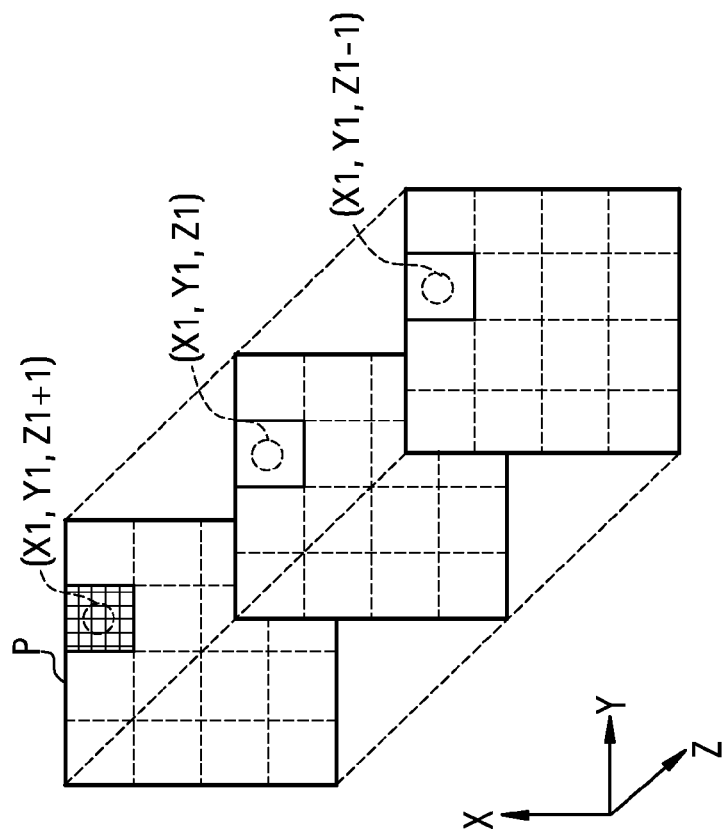
FIGS. 5(a) and 5(b) are conceptual diagrams showing pixels of tomographic images based on backprojection data D3 (x, y, z) and pixel areas thereof.
Figure 5A:
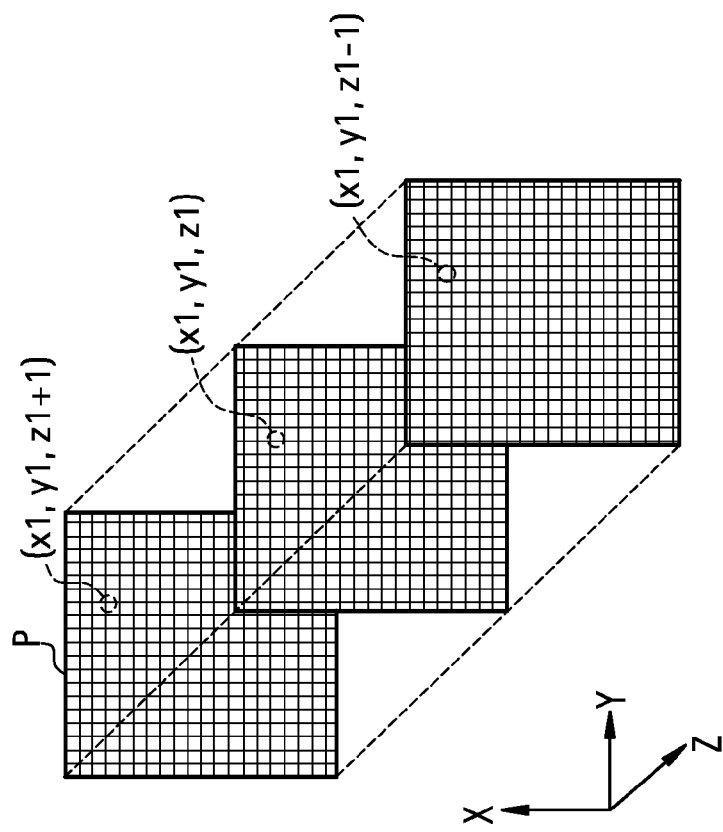

In FIG. 4(a), a z position of a subject HB that an operator wants to confirm is specified at Step S171. The artifact reduction unit 25 determines each pixel p (x, y, z) to be processed. If, for example, a square area of 512×512 pixels, which is parallel to the xy plane, is assumed to be a reconstruction area P as shown in FIG. 5(a), then x has a range from 1 to 512, and y also has a range from 1 to 512.

At Step S172, the CT value change specifying unit 26 measures a change in CT value as viewed in the z direction for each pixel p (x, y, z) to be processed. Assuming that, for example, changes in CT value in the z direction in the neighborhood of a pixel p (x1, y1, z1) to be processed in the reconstruction area P are as follows:

$p(x1, y1, z-1) = 10$ HU (Hounsfield unit)

$p(x1, y1, z) = 30$ HU $p(x1, y1, z+1) = 50$ HU

It is understood from this that the amount of change of 40 HU exists from the difference between the minimum CT value and the maximum CT value in the neighborhood of the p (x1, y1, z) in the body-axis direction.

Here, FIG. 5(a) shows z-direction pixels in the neighborhood of the pixel p (x1, y1, z1). The change in VT value will be explained below based on the premise of a change for each pixel. However, an average CT value in a pixel area (X1, Y1, Z1) in which a plurality of pixels around one specific pixel are combined together, may be adopted, or the highest CT value or lowest CT value may be used. A pixel area constituted of a plurality of pixels is moved with being shifted for each specific pixel. Although the amount of change in CT value of one slice in the neighborhood of the pixel p (x1, y1, z1) to be processed has been measured as above, the amounts of change in CT values of n slices in the neighborhood thereof may be measured.

Next, at Step S173, the CT value change specifying unit 26 determines an index. This index can be determined by the following function. In the following equation, changes in the CT values of the n slices in the neighborhood of the pixel p (x, y, z) to be processed are measured and the intended index is determined from the changes.

index=$f(p(x,y,z-n),p(x,y,z-n+1) \ldots p(x,y,z) \ldots p(x,y,z+n))$

It means that the index is set so as to reduce artifacts with respect to pixels in which the artifacts are being developed, whereas the index is set so as to take advantage of the pixel p (x, y, z) to be processed, as it is with respect to pixels with no artifacts developed therein. Functions for determining the indexes will be explained using FIGS. 7 and 8.

Assume that when the change in the CT value is given as p (x1, y1, z−1)=10 HU, p (x1, y1, z)=30 HU and p (x1, y1, z+1)=50 HU as the previous example, index=1 is reached.

Next, at Step S174, the artifact reduction unit 25 image-processes the pixel p (x, y, z) to be processed, based on the index value to determine a pixel p' (x, y, z) subsequent to its processing. For example, the pixel p' is expressed in the following equation 1:

[Equation 1]

$$p'(x, y, z) = \sum_{i=\text{start\_z}}^{\text{end\_z}} p(x, y, z+i) * g(i, \text{index}) \quad (1)$$

where g (i, index) is a weighting coefficient or factor of an ith slice in the z direction, based on the index. For example, the image processing condition selector 28 sets weighting factors every slice in the neighborhood of the pixel p (x1, y1, z1) to be processed, as follows:

Assume that when index=1, the weighting factor g applied or assigned to p (x1, y1, z−1) is g=0.33, the weighting factor g assigned to p (x1, y1, z) is g=0.33, and the weighting factor g assigned to p (x1, y1, z+1) is g=0.33. That is, each of pixels in which the artifacts are being developed is corrected to a pixel in which slices images in the neighborhood thereof are averaged. If n slice images are taken, then a value of g=1/(2n+1) may be used.

Assume that when index=0.5, the weighting factor g assigned to p (x1, y1, z−1) is g=0.2, the weighting factor g assigned to p (x1, y1, z) is g=0.6, and the weighting factor g assigned to p (x1, y1, z+1) is g=0.2. The influence of the pixel p (x, y, z) to be processed strongly remains in each pixel in which a weak artifact occurs, but slice images in the neighborhood of its pixel are also slightly added thereto.

Assume that when index=0, the weighting factor g assigned to p (x1, y1, z−1) is g=0, the weighting factor g assigned to p (x1, y1, z) is g=1, and the weighting factor g assigned to p (x1, y1, z+1) is g=0. The pixel p (x, y, z) to be processed is set to each pixel with no artifact so as to be used as it is.

Incidentally, the weighting factors g (i, index) may be stored in a lookup table or the like or stored as predetermined functions, based on information obtained from experiments or the like. Since the previous or subsequent slice does not exist, the weighting factor cannot be set to the initial or first slice or the final slice as described above. Therefore, there is a need to perform a correction process on the first slice or the final slice, using only each image in one side direction alone and also change the weighting factor.

At Step S175, a tomographic image D31 (x, y, z) is obtained based on the p' (x, y, z) subsequent to the artifact reducing or reduction process. Then, it is displayed on the display 60.

FIG. 6 is an example in which a tomographic image D3 (x, y, z) prior to execution of the artifact reduction process of the present embodiment and a tomographic image D31 (x, y, z) subjected to the artifact reduction process are displayed on the display 60. The windmill artifact and the cone-beam artifact are strongly displayed on the tomographic image D3 (x, y, z). However, the influences of the windmill artifact and the cone-beam artifact are reduced as in the case of the tomographic image D31 (x, y, z) shown in the right drawing. In the tomographic image D 31 (x, y, z) shown in the right drawing, a pixel area with no artifact becomes the same image as the tomographic image D3 (x, y, z) shown in the left drawing and remains same in resolution.

The flowchart shown in FIG. 4(*b*) is a flowchart using no index or index function (refer to FIG. 7 or FIG. 8) described at Step S173 of FIG. 4(*a*).

In the flowchart shown in FIG. 4(*b*), after the amount of change in CT value as viewed in the z direction has been measured for each pixel p (x, y, z) to be processed, at Step S172, a weighting factor gv is also determined based on the amount of change in CT value at Step S174' without determining the index in the next place.

At Step S174', the pixel p (x, y, z) to be processed is image-processed based on the index value to determine a pixel p' (x, y, z) subsequent to its processing. The pixel p' (x, y, z) is expressed in the following equation 2, for example:

[Equation 2]

$$p'(x, y, z) = \sum_{i=\text{start\_z}}^{\text{end\_z}} p(x, y, z+i) * gv(i, CTv) \quad (2)$$

where gv (i, CTv) is a weighting coefficient or factor of an ith slice in the z direction, based on the amount of change in CT value. For example, the image processing condition selector 28 sets weighting factors every slice in the neighborhood of the pixel p (x1, y1, z1) to be processed, as follows:

Assume that when the amount of change in CT value is 40 HU, the weighting factor gv applied or assigned to p (x1, y1, z−1) is gv=0.33, the weighting factor gv assigned to p (x1, y1, z) is gv=0.33, and the weighting factor gv assigned to p (x1, y1, z+1) is gv=0.33.

Assume that when the amount of change in CT value is 120 HU, the weighting factor gv assigned to p (x1, y1, z−1) is gv=0.2, the weighting factor gv assigned to p (x1, y1, z) is gv=0.6, and the weighting factor gv assigned to p (x1, y1, z+1) is gv=0.2.

Assume that when the amount of change in CT value is 200 HU, the weighting factor gv assigned to p (x1, y1, z−1) is gv=0, the weighting factor gv assigned to p (x1, y1, z) is gv=1.0, and the weighting factor g assigned to p (x1, y1, z+1) is gv=0.

Thus, the weighting factor gv may be determined directly from the amount of change in CT value. A method of directly determining the weighting factor gv needs to determine a large number of weighting factors gv every amount of change in CT value. Therefore, the quantities to be stored in the lookup table or the like depending upon the amount of change in CT value increase and the setting of the weighting factor gv becomes complex.

Example of index function.

Figure 8A:
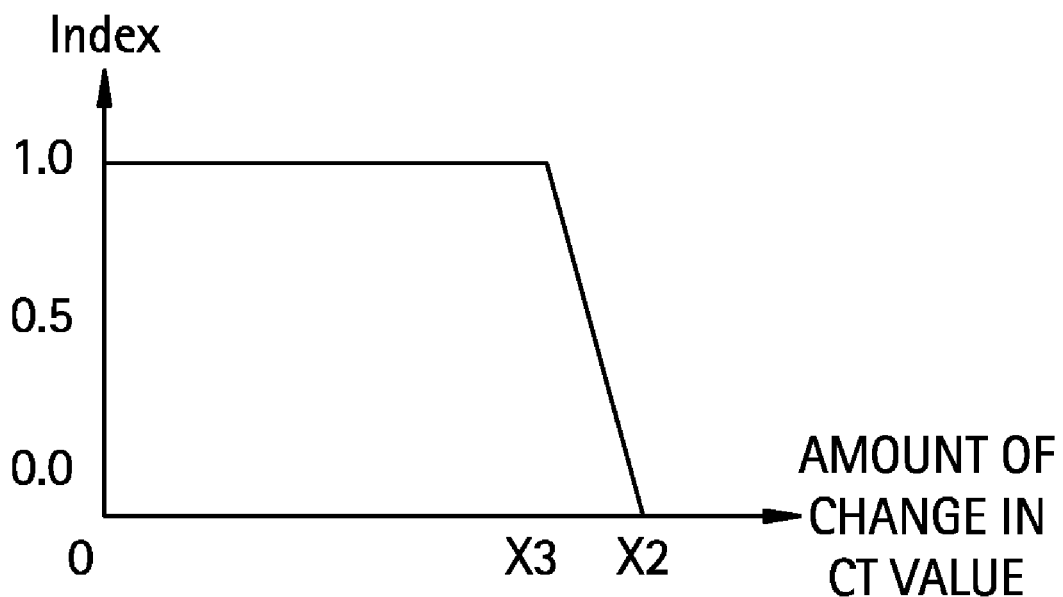
FIGS. 8(a) and 8(b) are diagrams illustrating other index functions.
Figure 8B:
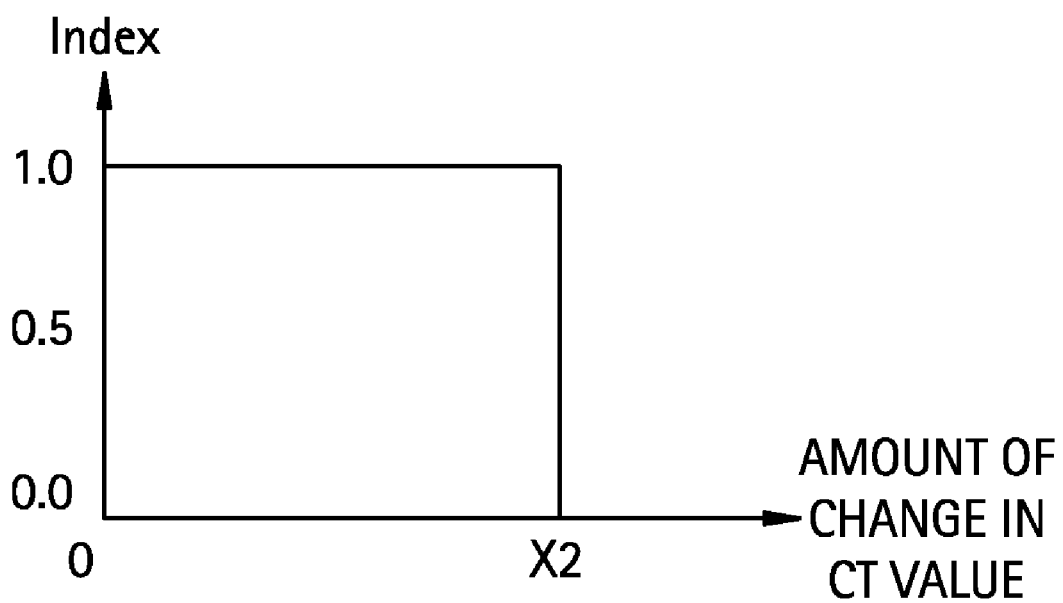

FIGS. 7 and 8 are diagrams showing index functions for determining the indexes used at Step S173 of FIG. 4.

The index function of FIG. 7(*a*) is a function in which if the amount of change in CT value ranges from X1 to X3, then the index linearly changes from 0 to 1, and if the amount of change in CT value ranges from X3 to X2, then the index linearly changes from 1 to 0. Assume that, for example, X1 is 10 HU, X3 is 90 HU and X2 is 170 HU. When p (x1, y1, z−1)=10 HU, p (x1, y1, z)=30 HU and p (x1, y1, z+1)=50 HU with respect to a given image to be processed, the amount of change in CT value is 40 HU. In such a case, index=0.5 is determined in the index function shown in FIG. 7(*a*).

X1, X2 and X3 are set from 3 HU to 300 HU to 10 UH to 200 HU depending upon an imaging condition. When they are 200 HU or more, it means a portion or region that has changed from a soft tissue to the bone or vice versa. If they are 10 HU or less, it then means that the soft tissue is continuous in plural slice directions or the bone is continuous in the plural slice directions. On the other hand, it is estimated from the change in CT value from 3 HU to 300 HU or the amount of change in CT value from 10 HU to 200 HU strictly that the windmill artifact or the cone-beam artifact is being developed. Incidentally, the setting of the amount of change in CT value can suitably be changed based on the resolution, slice thickness or table velocity or the like at the photography. If the amount of change in CT value in the body-axis direction ranges from 3 HU to 300 HU as a result of various experiments, it can then be estimated that the artifacts are being developed.

The index function of FIG. 7(*b*) is a function in which if the amount of change in CT value ranges from X1 to X3, then the index linearly changes from 0 to 1, if the amount of change in CT value ranges from X3 to X4, then the index remains at 1 as it is, and if the amount of change in CT value ranges from X4 to X2, then the index linearly changes from 1 to 0. Assume that, for example, X1 is 10 HU, X3 is 40 HU, X4 is 160 HU and X2 is 190 HU. According to the index function, if the amount of change in CT value ranges from 40 HU to 160 HU, it is then judged to be an artifact.

The index function of FIG. 7(*c*) is a function in which if the amount of change in CT value falls between X1 and X3, then the index changes into a curved form from 0 to 1, and if the amount of change in CT value falls between X3 and X2, then the index changes into a curved form from 1 to 0.

On the other hand, as to the index function of FIG. 7(*d*), if the amount of change in CT value falls between X1 and X2, then the index is 1 and 0 at other times. Therefore, if the amount of change in CT value is X1 or less or the amount of change in CT value is X2 or more, it then means that an image to be processed is used as a tomographic image as it is.

The index function of FIG. 8(*e*) is a function in which if the amount of change in CT value falls between 0 HU and X3, then the index is 1, and the if the amount of change in CT value falls between X3 and X2, then the index linearly changes from 1 to 0. As to the index function of FIG. 8(*f*), if the amount of change in CT value falls between 0 HU and X2, then the index is 1 and 0 at other times. Assume now that X3 ranges from 40 HU to 200 HU and X2 ranges from 80 HU to 300 HU.

Indicating that the amount of change in CT value is approximately 0 HU means that the same soft region or bone region is continuous in plural slice directions. Since the amount of change in CT value is approximately 0 HU and index=1.0, it means that the corresponding pixel is averaged with a predetermined weighting factor in accordance with the equation (1). That is, a noise reduction is done in the range in which the amount of change in CT value is from 0 HU to about 10 HU, without performing a reduction in artifact. That is, the index function of FIG. 8(*e*) or 8(*f*) performs the reduction in artifact using the equation (1) in the range in which the change in CT value is from over about 10 HU to under 200 HU or under 300 HU, and performs the noise reduction using the equation (1) in like manner in the case in which the amount of change in CT value is about 10 HU or less.

Although the index functions of (a) through (f) are shown in FIGS. 7 and 8 as above, one function need not necessarily be used. It is possible to change the index function depending on the position in the z direction. For example, the index function (a) may be used in a head region, the index function (c) may be used in a neck region, and the index function (e) may be used in a leg region. Even in the case of the flowchart shown in FIG. 4(*b*), the weighting factor gv may be set depending upon the z-direction position.

Specifying tomographic image in which artifacts exist.

It has been estimated in the above embodiment that when the amount of change in CT value is of the predetermined range at the pixel p (x1, y1, z1) or in the pixel area (X1, Y1, Z1) in which plural pixels around the pixel p are combined together, artifacts are developed in its pixel as shown in FIG. 5. The processing of the equation (1) or (2) has been effected on the pixel p (x1, y1, z1) to be processed. The following embodiment is one method of further enhancing specifying or determination of an area in which artifacts are being developed.

FIG. 9 is a diagram showing tomographic images prior to being subjected to an artifact reducing or reduction process, of the head of a subject, and reconstruction areas P. Many windmill artifacts exist in the upper stage tomographic image D3-A shown in FIG. 9(A1), and the windmill artifacts almost remain non-existent in the lower stage tomographic image D3-B shown in FIG. 9(B1). The reconstruction area P shown in FIG. 9 is a square area of 512×512 pixels, which is parallel to an xy plane. As a result of determination of indexes about the tomographic image D3-A and the tomographic image D3-B, pixels brought to index=1.0 are filled in. In the reconstruction area P shown in FIG. 9(A2), the artifact ratio obtained by dividing the number of pixels at index=1.0 by the entire number of pixels is 0.12. In the reconstruction area P shown in FIG. 9(B2), the artifact ratio obtained by dividing the number of pixels at index=1.0 by the entire number of pixels is 0.03. This calculation is performed by the artifact ratio calculator 27 shown in FIG. 1.

When the processing of the equation (1) or (2) is effected on each pixel of index=1.0 regardless of the fact that the windmill artifact remains almost non-existent in the tomographic image D3-B, the resolution in the z direction is reduced. Therefore, the artifact ratio calculator 27 checks for the artifact ratio corresponding to the ratio indicative of how pixels estimated to be index=1.0, i.e., to have developed the artifacts, of the entire pixels in the reconstruction area P is taken up or occupied. When the artifact ratio is larger than a predetermined threshold value SH, the determinator 29 effects the processing of the equation (1) or (2) on the tomographic image D3. That is, the decision that the artifact is recognized as being developed, is made more stringent.

Figure 10:
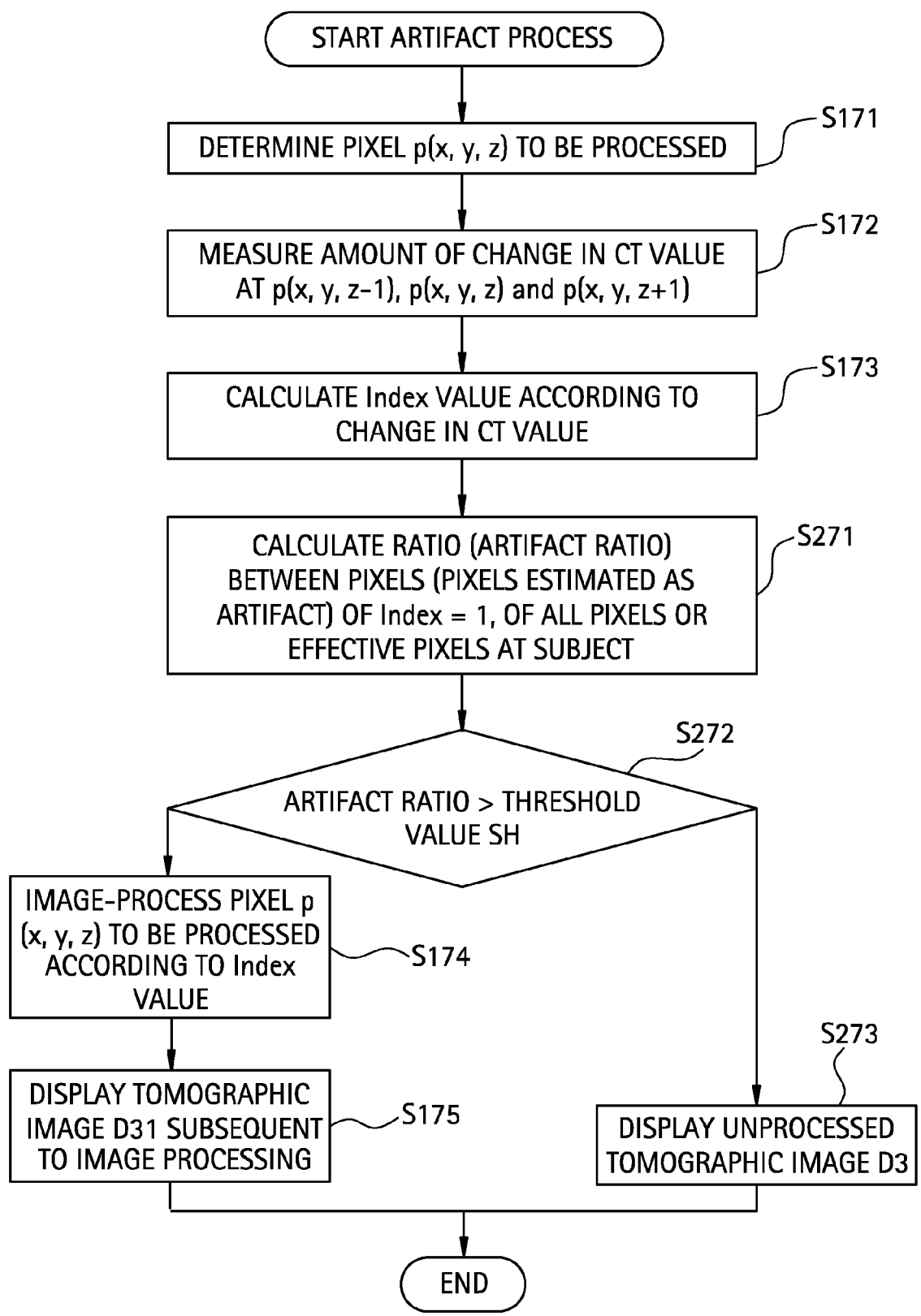
FIG. 10 is a diagram showing a flowchart for performing an artifact reduction process after examinations of artifact ratios.

FIG. 10 is a diagram showing a flowchart for performing an artifact reduction process after examinations of the artifact ratios. In the flowchart shown in FIG. 10, the same Steps as those in the flowchart of FIG. 4(*a*) for reducing the artifacts are assigned the same Step numbers. Explanations of the same Step numbers are partly omitted.

At Step S171, the z position of a subject HB that an operator wants to confirm is specified. The artifact reduction unit 25 determines a pixel p (x, y, z) to be processed.

At Step S172, a change in CT value in the z direction is measured at the pixel p (x, y, z) to be processed.

At Step S173, the index for the pixel p (x, y, z) to be processed is determined. If the reconstruction area P is of a square area of 512×512 pixels, then the amount of change in CT value in the z direction is measured in a range in which x is from 1 to 512 and a range in which y is also from 1 to 512.

Next, the artifact reduction process proceeds to Step S271 as a Step peculiar to FIG. 9. At Step S271, the artifact ratio calculator 27 calculates an artifact ratio. As to the artifact ratio, the ratio between pixels of index=1, of all the pixels (512×512) is calculated.

Incidentally, the area for the subject HB is specified in place of all pixels, and the ratio between pixels of index=1 may be calculated in the number of pixels in the area. In place of the ratio between the pixels of index=1, the ratio between points or spots of index=0.7 or more or index=0.5 or more may be calculated. The following description will be made of, as the artifact ratio, the ratio between the pixels of index=1, of all the pixels (512×512).

At Step S272, the determinator 29 determines whether the artifact ratio is larger than the threshold value SH. For example, the artifact ratio=0.07 is used as the threshold value SH. If the artifact ratio of a target tomographic image D3 is larger than the threshold value SH, then the determinator proceeds to Step S174. If this artifact ratio is smaller than the threshold value SH, then the determinator proceeds to Step S273.

At Step S174, the pixel p (x, y, z) to be processed is image-processed based on the index value in accordance with the above equation 1 to determine a pixel p' (x, y, z) subsequent to its processing. This calculation is performed on all the pixels (512×512) of the target tomographic image D3. At Step S175, a tomographic image D31 (x, y, z) is obtained based on the p' (x, y, z) subsequent to the artifact reduction process. Then, the tomographic image D31 (x, y, z) is displayed on the display 60 at Step S175.

On the other hand, at Step S273, the target tomographic image D3 is displayed on the display 60 while remaining unsubjected to any image processing. This is because although there is a possibility that the pixels of index=1 will cause the artifacts in the reconstruction area P, the artifacts are considered to be inconspicuous since the pixels of index=1 are low in number in the entire reconstruction area P, and such image processing as to decrease the resolution in the body-axis direction is undesirable.

Figure 11:
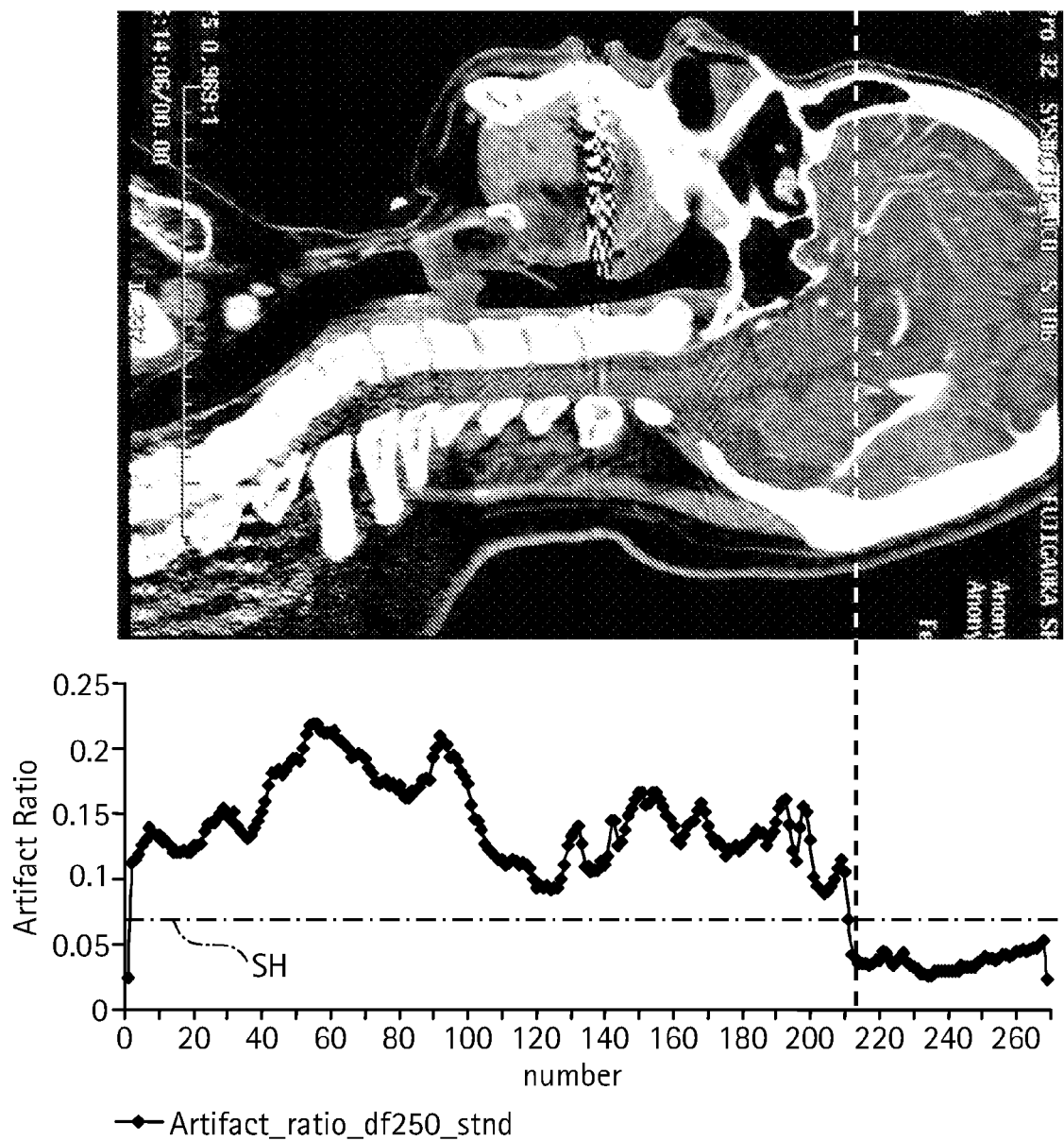
FIG. 11 is a cross-sectional view in a body-axis direction from the chest of a subject HB to the head thereof, and artifact ratios.

FIG. 11 is a cross-sectional view in a body-axis direction from the chest of a subject HB to the head thereof at its upper stage, and is a diagram showing the relationship between artifact ratios and the numbers of tomographic images arranged in the body-axis direction at its lower stage.

Looking at the relationship between the artifact ratios and the body-axis direction, the artifact ratio of the chest to the neighborhood (indicated by a white dotted line in FIG. 11) of the eyes or eyebrows of the head ranges from 0.9 to 2.2 or so. In the tomographic image D3 (x, y, z) prior to execution of the artifact reduction process of the present embodiment, the artifact ratio between the neighborhood of the eyes or eyebrows and the top of head ranges from 0.3 to 0.5 or so. As understandable from FIG. 11, the more the shape of a structure such as a bone becomes complex, the more the artifacts are easy to occur. When the shape of the bone or the like lying in the vicinity of the top of head is simple in reverse, the artifacts are hard to occur. In FIG. 11, the artifact ratio=0.07 is defined as the threshold value SH. Therefore, according to the flowchart of FIG. 10, the image processing of the equation 1 or the like is effected on the tomographic image D3 in the vicinity of the chest to the neighborhood of the eyes or eyebrows of the head. On the other hand, the image processing of the equation 1 or the like is not effected on part of the tomographic image D3 between the neighborhood of the eyes or eyebrows and the top of head even though the pixels of index=1 exist.

Incidentally, the image reconstructing method according to the present embodiment may be a three-dimensional image reconstructing method based on the Feldkamp method known to date. Further, another three-dimensional image reconstructing method may be adopted. Alternatively, a two-dimensional image reconstructing method may be adopted. Image quality determined as each region varies according to diagnostic applications, the preferences of an operator, etc. and exists in a wide variety of forms. Therefore, the operator may set the setting of an imaging condition most suitable for each region in advance.

Although the amount of change in CT value has been explained using the difference between the maximum and minimum CT values of one slice or plural slices in the neighborhood of the pixel p (x1, y1, z1) to be processed, it may be processed using the average amount of change in CT value obtained by dividing the difference between the maximum CT value and the minimum CT value by the number of slices.

The present embodiment is not limited to the specific scan form in particular. That is, similar effects can be brought about even in the case of an axial scan, a cine scan, a helical scan, a variable pith helical scan and a helical shuttle scan. The present embodiment is not limited to the tilt or gradient of the gantry 100. That is, similar effects can be brought about even in the case of a so-called tilt scan at which the gantry 100 is tilted. The present embodiment can be applied even to cardiac image reconstruction which image-reconstructs each image in sync with a biological signal, particularly, a cardiac signal.

Although the present embodiment has been described on the basis of the medical X-ray CT apparatus 10, it can be made available even to an X-ray CT-PET apparatus utilized in combination with an industrial X-ray CT apparatus or another apparatus, an X-ray CT-SPECT apparatus utilized in combination therewith, etc.

The invention claimed is:

1. An X-ray computed tomography (CT) apparatus comprising:
a scan device for exposing X rays to a subject while at least one of a gantry and a table is being moved along a body-axis direction of the subject, to create projection data of the subject;
a CT value change determining device for determining an amount of change in CT value in the body-axis direction between a plurality of tomographic images obtained by backprojecting the projection data, with respect to each of pixel areas contained in the tomographic images;
an image processing condition selecting device for estimating a range of an amount of change in CT value caused by an artifact, and for selecting an image processing condition for performing an image process for reducing artifacts based on whether the determined amount of change in CT value falls within the estimated range of the amount of change in CT value caused by an artifact, wherein the estimated range includes the amount of change in CT value smaller than that estimated to be caused by a structure of the subject and larger than that estimated to be caused by noise within the tomographic image; and an artifact reducing device for performing an image process using the image processing condition selected by the image processing condition selecting device.

2. The X-ray computed tomography apparatus according to claim 1, further including:

an artifact ratio calculating device for calculating a ratio of a number of pixel areas in which the amount of change in CT value is within a predetermined range, to a total number of pixel areas in each of the tomographic images; and a determining device for determining that when the ratio is larger than a threshold value, an image process for reducing the artifacts is effected on the pixel area.

3. The X-ray computed tomography apparatus according to claim 1, wherein the image process of the artifact reducing device includes a process for multiplying, a plurality of pixel areas in the body-axis direction of the tomographic images by weighting factors based on the image processing condition, and adding the results of the multiplication.

4. The X-ray computed tomography apparatus according to claim 3, wherein the image processing condition selecting device sets the weighting factor to be larger than 0 when the amount of change in CT value is within a predetermined range.

5. The X-ray computed tomography apparatus according to claim 3, wherein the image processing condition selecting device changes the weighting factor according to the number of the pixel areas in the body-axis direction.

6. The X-ray computed tomography apparatus according to claim 3, wherein the image processing condition selecting device changes the weighting factor according to the amount of change in CT value.

7. The X-ray computed tomography apparatus according to claim 1, wherein the CT value change determining device determines an index value based on the amount of change in CT value, the index value corresponding to a set of weighting factors.

8. The X-ray computed tomography apparatus according to claim 7, wherein plural pixel areas in the body-axis direction are multiplied by the weighting factors in relation to the pixel areas and the results of the multiplication are added together.

9. The X-ray computed tomography apparatus according to claim 2, wherein the predetermined range expressed in Hounsfield units (HU) is from 3 HU to 300 HU.

10. The X-ray computed tomography apparatus according to claim 1, wherein each of the pixel areas comprises one pixel or a plurality of pixels.

11. A method of reducing artifacts of X-ray computed tomographic (CT) images comprising:

determining an amount of change in CT value in a body-axis direction between a plurality of tomographic images obtained by backprojecting projection data of a subject obtained by exposing X rays to the subject while at least one of a gantry and a table is being moved along the body-axis direction of the subject, with respect to each of pixel areas contained in the tomographic images;

estimating a range of an amount of change in CT value caused by an artifact, wherein the estimated range includes the amount of change in CT value smaller than that estimated to be caused by a structure of the subject and larger than that estimated to be caused by noise within the tomographic image;

selecting an image processing condition for performing an image process to reduce artifacts based on whether the determined amount of change in CT value falls within the estimated range of the amount of change in CT value caused by an artifact; and performing an image process using the selected image processing condition.

12. The artifact reducing method according to claim 11, further comprising:

calculating a ratio of a number of pixel areas in which the amount of change in CT value is within a predetermined range, to a total number of pixel areas in each of the tomographic images; and determining that when the ratio is larger than a threshold value, the image process for reducing the artifacts is effected on each of the pixel areas.

13. The artifact reducing method according to claim 11, wherein the image process for reducing the artifacts includes a process for multiplying a plurality of pixel areas in the body-axis direction of the tomographic images by weighting factors based on the image processing condition, and adding the results of the multiplication.

14. The artifact reducing method according to claim 13, wherein the image processing condition selecting step sets the weighting factor to be larger than 0 when the amount of change in CT value is within a predetermined range.

15. The artifact reducing method according to claim 13, wherein the weighting factor is changed according to the number of the pixel areas in the body-axis direction.

16. The artifact reducing method according to claim 13, wherein the weighting factor is changed according to the amount of change in CT value.

17. The artifact reducing method according to claim 11, wherein an index value is determined based on the determined amount of change in CT value, the index value corresponding to a set of weighting factors.

18. The artifact reducing method according to claim 13, wherein the weighting factor is changed according to each region of the subject.

19. The artifact reducing method according to claim 11, wherein when the amount of change in CT value expressed in Hounsfield units (HU) ranges from 3 HU to 300 HU, an artifact is reduced with respect to each of the pixel areas.

20. The artifact reducing method according to claim 11, wherein when the amount of change in CT value expressed in Hounsfield units (HU) ranges from 0 HU to 300 HU, an artifact is reduced with respect to each of the pixel areas and noise is reduced with respect to the pixel area.

* * * * *